United States Patent [19]

Jikihara et al.

[11] 4,420,327
[45] Dec. 13, 1983

[54] TETRAHYDROPHTHALIMIDES AND HERBICIDAL COMPOSITION

[75] Inventors: Tetsuo Jikihara, Kawasaki; Masatsugu Oda, Yokohama; Kazuyuki Ushinohama, Yokohama; Hisao Watanabe, Yokohama; Seiichi Suzuki, Yokohama, all of Japan

[73] Assignee: Mitsubishi Chemical Industries Ltd., Tokyo, Japan

[21] Appl. No.: 308,824

[22] Filed: Oct. 5, 1981

[30] Foreign Application Priority Data

Oct. 7, 1980 [JP] Japan ................................ 55-140074
Oct. 9, 1980 [JP] Japan ................................ 55-141777

[51] Int. Cl.$^3$ .................... A01N 43/38; C07D 209/48
[52] U.S. Cl. .......................................... 71/96; 71/90; 548/407; 548/465; 548/513
[58] Field of Search ...................... 548/407, 513, 465; 71/90, 96

[56] References Cited

U.S. PATENT DOCUMENTS

| | | | |
|---|---|---|---|
| 3,878,224 | 4/1975 | Matsui et al. ........................... | 71/94 |
| 3,984,435 | 10/1976 | Matsui et al. ........................... | 71/96 |
| 4,001,272 | 1/1977 | Goddard .............................. | 548/476 |
| 4,157,256 | 6/1979 | Hiraga et al. ........................... | 71/95 |
| 4,292,070 | 9/1981 | Wakabayashi et al. ................ | 71/96 |

*Primary Examiner*—Donald G. Daus
*Assistant Examiner*—M. C. Eakin
*Attorney, Agent, or Firm*—Oblon, Fisher, Spivak, McClelland & Maier

[57] ABSTRACT

$\Delta'$-Tetrahydrophthalimides having a substituted oxy group at 3-position and a halogen atom at 4-position if necessary, a halogen atom at 2-position of phenyl group as N-substituent have excellent herbicidal activity and are useful as selective herbicides.

31 Claims, No Drawings

TETRAHYDROPHTHALIMIDES AND HERBICIDAL COMPOSITION

BACKGROUND OF THE INVENTION

The present invention relates to novel N-substituted tetrahydrophthalimides and herbicidal compositions thereof.

N-substituted aryl-Δ'-tetrahydrophthalimide derivatives having herbicidal activity have been reported.

For example, Japanese Examined Patent Publication No. 11940/1973 (U.S. Pat. No. 3,878,224 and U.S. Pat. No. 3,984,435 and West German Unexamined Patent Publication 2,165,651) discloses N-substituted-Δ'-tetrahydrophthalimide which is represented by the general formula

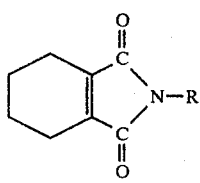

wherein R may be an aryl or aralkyl as phenyl optionally substituted with 1 to 5 halogen atoms; hydroxy, alkoxy, nitro, cyano, thiocyanno, carboxy, halogenated alkyl, alkyl, phenyl and OCH$_2$A (wherein A is phenyl or naphthyl) group and the like may also be substituted therein. N-(4-chloro-3-methoxyphenyl)-Δ'-tetrahydrophthalimide and N-(4-bromo-3-methoxyphenyl)-Δ'-tetrahydrophthalimide are described as the exemplified compounds having the formula wherein R is a halogen- and alkoxy-substituted phenyl group.

U.S. Pat. No. 4,001,272 and U.S. Pat. No. 4,032,326 disclose herbicidal 2-substituted aryl-4,5,6,7-tetrahydro-2H-isoindole-1,3-diones of the following formula:

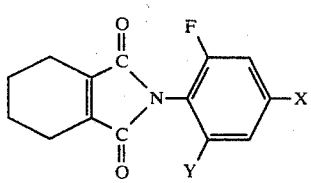

wherein X is Cl, Br or F and Y is H or F.

The activity of these compounds is very substantially affected by the type of substituents encompassed by the above generic formula, the number of these substituents and the structural positions of the substituents. Thus, it is difficult to predict herbicidal effects of novel compounds in view of similarity of chemical structures.

The inventors have studied novel tetrahydrophthalimides as an active ingredient of a herbicidal composition and have found that the specific novel N-aryl-3,4,5,6-tetrahydrophthalimides having H or a halogen atom at 2-position, a halogen atom at 4-position and a specific substituent at 5-position have excellent herbicidal effect.

SUMMARY OF THE INVENTION

The present invention is to provide novel N-substituted 3,4,5,6-tetrahydrophthalimides which are represented by the general formula

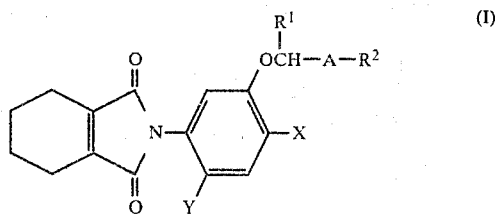

wherein X represents hydrogen or a halogen atom; Y represents hydrogen or a halogen atom; $R^1$ represents hydrogen atom or an alkyl group; $R^2$ represents hydrogen atom or an alkyl or phenyl group or $R^1$ and $R^2$ are connected to form

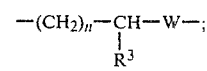

$R^3$ represents hydrogen atom or an alkyl group; W represents —O— or —CH$_2$—; n represents an integer of 1 or 2; A represents

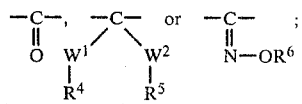

$W^1$ and $W^2$ represents —O— or —S—; $R^4$ and $R^5$ can be the same or different and respectively represent an alkyl group or $R^4$ and $R^5$ can be connected to form an alkylene group; $R^6$ represents hydrogen atom, an alkyl, alkenyl, alkynyl, acyl, alkoxycarbonyl, carbamoyl or substituted carbamoyl group.

DETAILED DESCRIPTION OF THE PREFERRED EMBODIMENTS

The compounds having the formula (I) of the present invention are novel compounds. The typical compounds as herbicides can be the compounds having the formula (I) wherein X represents Cl or Br; Y represents H or Cl (preferably Y is H when X is Cl or Br and Y is Cl when X is Cl); $R^1$ represents H or a C$_{1-8}$ alkyl group such as methyl, ethyl, propyl, butyl, pentyl, hexyl, heptyl or octyl group, preferably a C$_{1-6}$ alkyl group such as methyl, ethyl, propyl, butyl, pentyl or hexyl group, especially a C$_{1-4}$ alkyl group; $R^2$ represents H, a C$_{1-4}$ alkyl group or phenyl group, preferably methyl or ethyl group as the alkyl group; $R^1$ and $R^2$ can connect to form

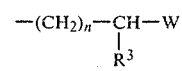

and $R^3$ represents H or an alkyl group preferably methyl group; W represents —O— or —CH$_2$—; n is 1 or 2; and A represents

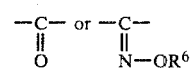

wherein $R^6$ represents H, a C$_{1-6}$ alkyl group such as methyl, ethyl, propyl, butyl, pentyl or hexyl group, preferably a C$_{1-4}$ alkyl group; or an acyl group such as acetyl, chloroacetyl, propionyl, butyryl, valeryl, acryloyl, methacryloyl and benzoyl group; a $C_{2-5}$ alkoxycarbonyl group such as methoxycarbonyl, ethoxycarbonyl, propoxycarbonyl and butoxycarbonyl group; non-substituted or substituted carbamoyl group such as carbamoyl, methylcarbamoyl, dimethylcarbamoyl, ethylcarbamoyl, diethylcarbamoyl, butylmethylcarbamoyl, ethylbutylcarbamoyl and phenylcarbamoyl group; a lower alkenyl group such as allyl group and an alkynyl group such as propargyl group; A can be

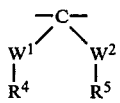

wherein $W^1$ and $W^2$ repectively represent —O— or —S— and $R^4$ and $R^5$ respectively represent a lower alkyl group such as methyl, ethyl or propyl or butyl group; or a lower alkylene group formed by connecting each other.

The compounds having the formula (I) can be various isomers such as optical isomers, diastereoisomers and Z-E isomers. These isomers and mixtures are included in the definition of the present invention. These isomers are usually obtained in the form of a mixture thereof. In the example, mixtures of the isomers are formed otherwise specified.

These isomers can be separated by various processes such as asymmetric synthesis, optical resolution, and various chromatography such as column chromatography, thin layer chromatography and high speed liquid chromatography.

The compounds having the formula (I) can be produced by the following processes:

Process (1)

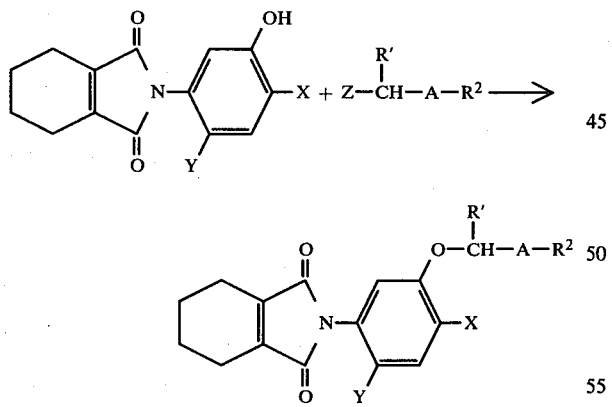

wherein X, Y, $R^1$, $R^2$ and A are defined in the formula (I) and Z represents a halogen atom.

The reaction is carried out in a solvent such as acetone, ethyl methyl ketone, benzene, toluene, acetonitrile, tetrahydrofuran and N,N-dimethylformamide in the presence of a base such as sodium carbonate, potassium carbonate, sodium hydroxide and potassium hydroxide or a fluoride such as potassium fluoride, cesium fluoride and tetra-n-butyl ammonium fluoride in the presence or absence of an iodide such as sodium iodide and potassium iodide at 0° to 150° C.

Process (2)

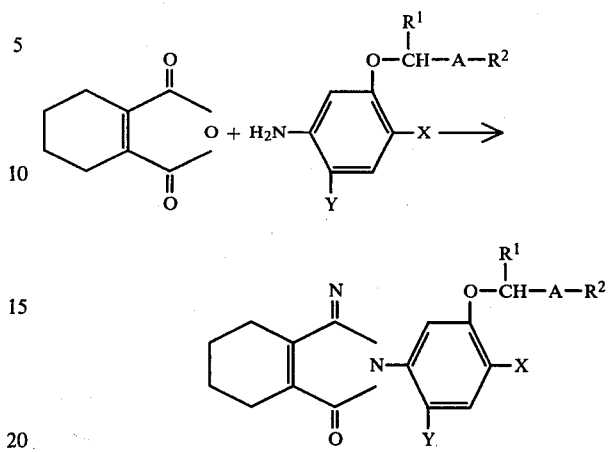

wherein X, Y, $R^1$, $R^2$ and A are defined in the formula (I).

The reaction of cyclohexene-1,2-dicarboxylic anhydride with the aniline is carried out without a solvent or in a solvent such as acetic acid, toluene, dioxane, methanol and water at 60° to 200° C.

Process (3)

The compounds having the formula (I) wherein A is

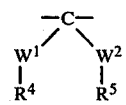

are preferably produced by the following process:

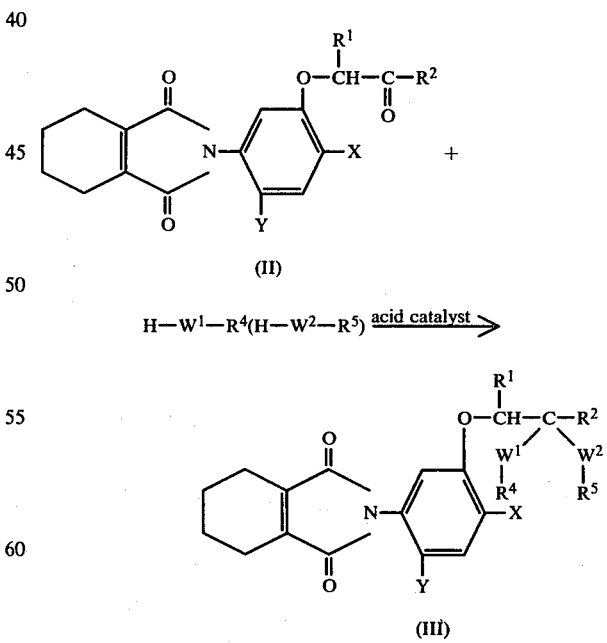

The compounds having the formula (II) can be obtained by the process (1) or (2).

The reaction can be carried out without a solvent or in a solvent such as benzene, toluene, xylene, methylene chloride, chloroform and carbon tetrachloride in the presence of a catalyst such as p-toluene sulfonic acid, methanesulfonic acid, hydrogen chloride, sulfuric acid, boron trifluoride etherate, zinc chloride and aluminum chloride at −10° to 180° C.

Process (4)

The compounds having the formula (I) wherein A is

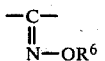

are preferably produced by the following process:

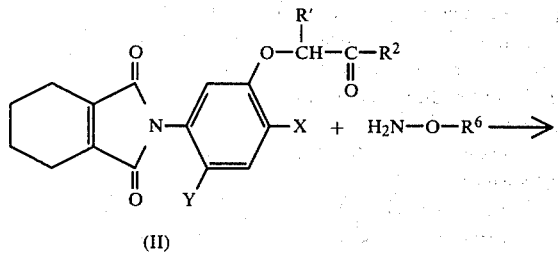

In accordance with the reaction of the ketone (II) with the hydroxylamine, the anilines having the formula (V) are produced. Tetrahydrophthalic anhydride is added to the product for the imidation to obtain the object compound (IV).

The reactions can be continuously carried out without an isolation of the aniline as the intermediate though the aniline can be isolated.

In the reaction, the intermediate is produced in a solvent such as methanol, ethanol, isopropanol, benzene, toluene and tetrahydrofuran at 20° to 140° C. and then, the reaction of the intermediate with tetrahydrophthalic anhydride is carried out without a solvent or in a solvent such as acetic acid, toluene, dioxane, methanol and water at 60° to 200° C.

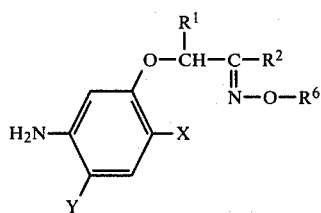

The processes for producing the compounds (I) of the present invention will be illustrated by certain examples which are provided for purposes of illustration only and are not intended to be limiting the present invention.

EXAMPLE 1

Production of N-[4-bromo-3-(γ-butyrolacton-3-yloxy)phenyl]-3,4,5,6-tetrahydrophthalimide A mixture of 3.0 g. of N-(4-bromo-3-hydroxyphenyl)-3,4,5,6-tetrahydrophthalimide, 2.3 g. of α-bromo-γ-butyrolactone, 1.5 g. of potassium carbonate, 1.5 g. of potassium iodide and 25 ml. of acetone was refluxed with stirring for 3 hours and then, the reaction mixture was cooled to room temperature and the precipitated salt was filtered. The filtrate was concentrated under a reduced pressure. 2 N-HCl was added to the residue and the product was extracted with ethyl acetate. The extract was washed with water and dried over sodium sulfate and then, sodium sulfate was separated by a filtration and the solvent was distilled off. The residue was purified by a chromatography on a column of silica gel (developing solvent: ethyl acetate:n-hexane of 1:3) to obtain 2.8 g. of Compound No. 3 shown in Table 1.

Compounds Nos. 1, 2, 4 to 6 and 10 to 13 were respectively produced by the similar process.

EXAMPLE 2

Production of N-[4-chloro-3-(cyclopentanon-2-yloxy)phenyl]-3,4,5,6-tetrahydrophthalimide A mixture of 1.52 g. of cyclohexene-1,2-dicarboxylic anhydride, 2.26 g. of 4-chloro-3-(cyclopentanon-2-yloxy) aniline and 10 ml. of acetic acid was stirred at room temperature for 30 minutes and then was refluxed with stirring for 2.5 hours. The solvent was distilled off under a reduced pressure and then, ethyl acetate was added to the residue to extract the product. The extract was washed with water and dehydrated over sodium sulfate. The solvent was distilled off and the product was purified by a chromatography on a column of silica gel (developing solvent: ethyl acetate:n-hexane of 1:4) to obtain Compound No. 5 shown in Table 1.

EXAMPLE 3

Production of N[4-bromo-3-(2,2-ethylenedioxycyclopentyloxy)-phenyl]-3,4,5,6-tetrahydrophthalimide A mixture of 2.2 g. of N-[4-bromo-3-(cyclopentanon-2-yloxy)phenyl]-3,4,5,6-tetrahydrophthalimide, 0.68 g. of ethyleneglycol, 0.2 g. of p-toluenesulfonic acid and 30 ml. of benzene was refluxed with stirring under removing water for 8 hours and the reaction mixture was cooled to room temperature and then, 20 ml. of ethyl acetate was added to the reaction mixture to extract the product. The extract was washed with water and dehydrated over sodium sulfate and the solvent was distilled off and the product was purified by a chromatography on a column of silica gel (developing solvent: ethyl acetate:n-hexane of 1:4) to obtain 1.35 g. of Compound No. 9 shown in Table 1.

Compounds Nos. 7 and 8 were also produced by the similar process.

EXAMPLE 4

Production of N-[4-bromo-3-(1-methyl-2-oxopropoxy)phenyl]-3,4,5,6-tetrahydrophthalimide A mixture of 4.0 g. of N-(4-bromo-3-hydroxyphenyl)-3,4,5,6-tetrahydrophthalimide, 2.0 g. of 3-chloro-2-butanone, 2.1 g. of potassium carbonate, 1.0 g. of potassium iodide and 30 ml. of acetone was refluxed with stirring for 3 hours. The precipitate was separated by a filtration and the filtrate was concentrated under a reduced pressure and the residue was purified by a chromatography on a column of silica gel (developing solvent: ethyl acetate:n-hexane of 2:3) to obtain 4.2 g. of Compound No. 24 shown in Table 1.

Compounds Nos. 14 to 17, 23, 25, 42, 43, 45, 48, 59 and 60 were respectively produced by the similar process.

EXAMPLE 5

Production of N-[4-bromo-3-(1-propyl-2,2-ethylenedioxypropoxy)-phenyl]-3,4,5,6-tetrahydrophthalimide A mixture of 1.5 g. of N-[4-bromo-3(1-propyl-2-oxopropoxy)phenyl]-3,4,5,6-tetrahydrophthalimide, 0.7 g. of ethyleneglycol, 0.1 g. of p-toluenesulfonic acid and 30 ml. of benzene was refluxed with stirring under removing water for 5.5 hours and the reaction mixture was cooled to room temperature and 0.4 ml. of triethylamine was added. The solvent was distilled off under a reduced pressure. The residue was purified by a chromatography on a column of silica gel (developing solvent: ethyl acetate:n-hexane:triethylamine of 30:80:1) to obtain 1.2 g. of Compound No. 49 shown in Table 1.

Compounds Nos. 18, 20, 27, 29, 30, 44, 53, 54, 62, 63 and 67 were respectively produced by the similar process.

EXAMPLE 6

Production of N-[4-bromo-3-(2,2-ethylenedithiopropoxy)phenyl]-3,4,5,6-tetrahydrophthalimide A mixture of 3.0 g. of N-[4-bromo-3-(2-oxopropoxy)phenyl]-3,4,5,6-tetrahydrophthalimide, 1.0 g. of dithioglycol, 2 droplets of borontrifluoride diethyl etherate, 6.0 g. of anhydrous magnesium sulfate and 50 ml. of a mixture of benzene and ether (3:2) was stirred at room temperature for 5 hours and the insoluble components were separated by a filtration. The filtrate was concentrated under a reduced pressure. The residue was purified by a chromatography on a column of silica gel (developing solvent: ethyl acetate:n-hexane of 3:7) to obtain 3.1 g. of Compound No. 19 shown in Table 1.

Compounds Nos. 28, 50, 52, 61 and 64 were respectively produced by the similar process.

EXAMPLE 7

Production of N-[4-chloro-3-(2-hydroxyimino-1-propylpropoxy)-phenyl]-3,4,5,6-tetrahydrophthalimide A mixture of 1.52 g. of cyclohexene-1,2-dicarboxylic anhydride, 2.57 g. of 3-(5-amino-2-chlorophenoxy)-hexan-2-one oxime ($n_D^{25}$=1.5506) and 8 ml. of acetic acid was refluxed for 2.5 hours and the reaction mixture was cooled to room temperature and the product was extracted with ethyl acetate and was washed with water and was dehydrated over sodium sulfate. The product was purified by a chromatography on a column of silica gel (developing solvent: ethyl acetate:n-hexane of 1:3) to obtain 3.53 g. of Compound No. 68 shown in Table 1.

EXAMPLE 8

Production of N-[4-bromo-3-(2-hydroxyimino-1-methylpropoxy)-phenyl]-3,4,5,6-tetrahydrophthalimide A mixture of 10.0 g. of 4-[4-bromo-3-(1-methyl-2-oxopropoxy)phenyl]-3,4,5,6-tetrahydrophthalimide, 5.3 g. of hydroxylamine hydrochloride, 10.7 g. of sodium bicarbonate and 70 ml. of ethanol was refluxed with stirring for 30 minutes. The precipitate was separated by a filtration. The filtrate was concentrated under a reduced pressure and 11.6 g. of cyclohexene-1,2-dicarboxylic acid and 50 ml. of acetic acid were added and the mixture was refluxed with stirring for 3 hours. The reaction mixture was concentrated under a reduced pressure and the product was extracted with ethyl acetate and the extract was washed with water and dehydrated over sodium sulfate. The solvent was distilled off and the residue was purified by a chromatography on a column of silica gel (developing solvent: ethyl acetate:n-hexane of 1:3) to obtain 13.6 g. of Compound No. 32 shown in Table 1.

Compounds Nos. 21, 22, 31, 33 and 69 to 71 were respectively produced by the similar process.

EXAMPLE 9

Production of N-[4-bromo-3-(2-allyloxyimino-1-methylpropoxy)-phenyl]-3,4,5,6-tetrahydrophthalimide Into a suspension of 0.24 g. of 50% NaH in 15 ml. of anhydrous tetrahydrofuran, 2.0 g. of N-[4-bromo-3-(3-hydroxyimino-1-methylpropoxy)phenyl]-3,4,5,6-tetrahydrophthalimide was gradually added at room temperature and the mixture was further stirred for 30 minutes and then 0.59 g. of allyl bromide was added to react them at room temperature for 3 hours. The precipitate was separated by filtration. The filtrate was concentrated under a reduced pressure and the product was extracted with ethyl acetate and the extract was washed with water and dehydrated over sodium sulfate. The solvent was distilled off and the residue was purified by a chromatography on a column of silica gel (developing solvent: ethyl acetate:n-hexane of 1:3) to obtain 1.3 g. of Compound No. 37 shown in Table 1.

Compounds Nos 34 to 36, 38 to 40, 55 to 58, 65 and 66 were respectively produced by the similar process.

EXAMPLE 10

Production of N-[4-bromo-3-(2-phenylcarbamoyloxyimino-1-methylpropoxy)phenyl]-3,4,5,6-tetrahydrophthalimide Into a solution of 1.0 g. of N-[4-bromo-3-(2-hydroxyimino-1-methylpropoxy)phenyl]-3,4,5,6-tetraphthalimide in 20 ml. of benzene, 0.81 g. of phenyl isocyanate was added and the mixture was kept at room temperature for 2 hours. The solvent was distilled off under a reduced pressure and the residue was purified by a chromatography on a column of silica gel (developing solvent: ethyl acetate: n-hexane of 1:3) to obtain 0.7 g. of Compound No. 41 shown in Table 1.

The structures of all of the compounds shown in Table 1 were confirmed by IR spectrum and/or $^1$H-NMR spectrum.

TABLE 1

[Structure: tetrahydrophthalimide N-linked to phenyl with meta-OCH(R¹)-A-R² substituent]

| No. | X | Y | —OCH(R¹)—A—R² | m.p. or nD |
|---|---|---|---|---|
| 1 | H | H | 3-oxotetrahydrofuran-2-yloxy (γ-butyrolactone-2-yloxy) | mp 161–163° C. |
| 2 | Cl | H | γ-butyrolactone-2-yloxy | mp 61–63° C. |
| 3 | Br | H | γ-butyrolactone-2-yloxy | mp 56–57° C. |
| 4 | Cl | Cl | γ-butyrolactone-2-yloxy | mp 169–170° C. |
| 5 | Cl | H | 3-oxocyclopentyloxy | mp 123–125° C. |
| 6 | Br | H | 3-oxocyclopentyloxy | amorphous solid |
| 7 | Br | H | 3,3-diethoxycyclopentyloxy (H₅C₂O, OC₂H₅) | mp 125–125.5° C. |
| 8 | Cl | H | cyclopentyloxy with spiro-1,3-dioxolane | mp 89–90° C. |
| 9 | Br | H | cyclopentyloxy with spiro-1,3-dioxolane | mp 133–134° C. |
| 10 | Cl | H | 5-methyl-γ-butyrolactone-2-yloxy (CH₃) | amorphous solid |
| 11 | Br | H | 5-methyl-γ-butyrolactone-2-yloxy (CH₃) | amorphous solid |
| 12 | Cl | H | 2-oxocyclohexyloxy | mp 132.5–133.5° C. |
| 13 | Br | H | 2-oxocyclohexyloxy | mp 139–141° C. |
| 14 | Cl | H | —O—CH(CH₃)—CH(OC₂H₅)₂ | mp 58–60° C. |
| 15 | Cl | H | —O—CH₂—COCH₃ | mp 115–117° C. |
| 16 | Br | H | —O—CH₂—CO—CH₃ | mp 138.5–140° C. |
| 17 | Cl | Cl | —O—CH₂—CO—CH₃ | mp 138–140° C. |
| 18 | Br | H | —O—CH₂—C(CH₃)(O—CH₂—CH₂—O) [1,3-dioxolan-2-yl] | mp 94–96° C. |
| 19 | Br | H | —O—CH₂—C(CH₃)(S—CH₂—CH₂—S) [1,3-dithiolan-2-yl] | mp 117–122° C. |
| 20 | Br | H | —O—CH₂—C(CH₃)(O—CH₂—CH₂—CH₂—O) [1,3-dioxan-2-yl] | mp 117–118.5° C. |
| 21 | Cl | H | —O—CH₂—C(=N—OH)—CH₃ | mp 137–141° C. |

TABLE 1-continued

[Structure: tetrahydrophthalimide N-linked to phenyl ring bearing -OCH(R¹)-A-R² substituent]

| No. | X | Y | -OCH(R¹)-A-R² | m.p. or n_D |
|---|---|---|---|---|
| 22 | Br | H | -O-CH₂-C(=N-OCH₃)-CH₃ | mp 102–104° C. |
| 23 | Cl | H | -O-CH(CH₃)-C(=O)-CH₃ | mp 97–97.5° C. |
| 24 | Br | H | -O-CH(CH₃)-C(=O)-CH₃ | mp 104–106° C. |
| 25 | Cl | Cl | -O-CH(CH₃)-C(=O)-CH₃ | mp 117.5–118.5° C. |
| 26 | Br | H | -O-CH(CH₃)-C(OC₂H₅)(CH₃)(OC₂H₅) | mp 107–110° C. |
| 27 | Br | H | -O-CH(CH₃)- (1,3-dioxolane with CH₃) | mp 148–149° C. |
| 28 | Br | H | -O-CH(CH₃)- (1,3-dithiolane with CH₃) | mp 144–145° C. |
| 29 | Cl | H | -O-CH(CH₃)- (1,3-dioxolane with two CH₃) | amorphous solid |
| 30 | Br | H | -O-CH(CH₃)- (1,3-dioxane with CH₃) | mp 148–148.5° C. |
| 31 | Cl | H | -O-CH(CH₃)-C(=N-OH)-CH₃ | mp 133–135° C. |
| 32 | Br | H | -O-CH(CH₃)-C(=N-OH)-CH₃ | mp 133–136° C. |
| 33 | Br | H | -O-CH(CH₃)-C(=N-OCH₃)-CH₃ | mp 142–143° C. |
| 34 | Cl | H | -O-CH(CH₃)-C(=N-OC₃H₇-n)-CH₃ | mp 100–102° C. |
| 35 | Br | H | -O-CH(CH₃)-C(=N-OC₃H₇-n)-CH₃ | mp 103–104° C. |
| 36 | Cl | H | -O-CH(CH₃)-C(=N-OCH₂CH=CH₂)-CH₃ | mp 118–119° C. |
| 37 | Br | H | -O-CH(CH₃)-C(=N-OCH₂CH=CH₂)-CH₃ | mp 115–115.5° C. |
| 38 | Br | H | -O-CH(CH₃)-C(=N-OCOCH₃)-CH₃ | $n_D^{25.5}$ 1.5637 |
| 39 | Br | H | -O-CH(CH₃)-C(=N-OCO-C₆H₅)-CH₃ | mp 166–167° C. |
| 40 | Br | H | -O-CH(CH₃)-C(=N-OCOC₂H₅)-CH₃ | mp 137–138° C. |
| 41 | Br | H | -O-CH(CH₃)-C(=N-OCONH-C₆H₅)-CH₃ | mp 111–112° C. |
| 42 | Cl | H | -O-CH(CH₃)-CO-C₆H₅ | mp 87–91° C. |
| 43 | Br | H | -O-CH(CH₃)-CO-C₆H₅ | mp 80–82° C. |
| 44 | Cl | H | -O-CH(CH₃)- (1,3-dioxolane with C₆H₅) | mp 125–126° C. |
| 45 | Cl | H | -O-CH(C₂H₅)-CO-CH₃ | mp 67.5–68.5° C. |
| 46 | Br | H | -O-CH(C₂H₅)-COCH₃ | mp 71.5–72.5° C. |
| 47 | Cl | H | -O-CH(C₃H₇-n)-COCH₃ | mp 95–97° C. |
| 48 | Br | H | -O-CH(C₃H₇-n)-COCH₃ | mp 68.5–71° C. |

TABLE 1-continued

Structure: 3,4,5,6-tetrahydrophthalimide N-substituted with phenyl bearing –OCH(R¹)–A–R² group

| No. | X | Y | –OCH(R¹)–A–R² | m.p. or $n_D$ |
|---|---|---|---|---|
| 49 | Br | H | R¹ = C₃H₇-n; A–R² = 1,3-dioxolan-2-yl-CH₃ (–O–CH(C₃H₇-n)–C(O,O-ring)–CH₃) | mp 84–88.5° C. |
| 50 | Cl | H | R¹ = C₃H₇-n; 1,3-dithiolan-2-yl-CH₃ | mp 126–129° C. |
| 51 | Br | H | R¹ = C₃H₇-n; 1,3-dithiolan-2-yl-CH₃ | mp 108–113° C. |
| 52 | Br | H | R¹ = C₃H₇-n; –C(SC₂H₅)(S-C₂H₅)–CH₃ | amorphous solid |
| 53 | Br | H | R¹ = C₃H₇-n; 4,4-dimethyl-1,3-dioxolan-2-yl (–C(CH₃)(CH₃) with O,O) | amorphous solid |
| 54 | Br | H | R¹ = C₃H₇-n; 1,3-dioxan-2-yl-CH₃ (6-membered) | amorphous solid |
| 55 | Cl | H | R¹ = C₃H₇-n; –C(=N–OC₄H₉-n)–CH₃ | $n_D^{25}$ 1.5387 |
| 56 | Cl | H | R¹ = C₃H₇-n; –C(=N–OCOC₃H₇-n)–CH₃ | $n_D^{25}$ 1.5400 |
| 57 | Cl | H | R¹ = C₃H₇-n; –C(=N–OCOOC₄H₉-n)–CH₃ | $n_D^{25}$ 1.5491 |
| 58 | Br | H | R¹ = C₃H₇-n; –C(=N–OCON(CH₃)₂)–CH₃ | $n_D^{25}$ 1.5613 |
| 59 | Cl | H | R¹ = C₄H₉-n; –O–CH(C₄H₉-n)–COCH₃ | mp 66–67.5° C. |
| 60 | Br | H | R¹ = C₄H₉-n; –O–CH(C₄H₉-n)–COCH₃ | mp 69–70.5° C. |
| 61 | Cl | H | R¹ = C₄H₉-n; –C(SC₂H₅)(S-C₂H₅)–CH₃ | $n_D^{25}$ 1.5582 |
| 62 | Br | H | R¹ = C₄H₉-n; 1,3-dioxolan-2-yl-CH₃ | $n_D^{25}$ 1.5545 |
| 63 | Cl | H | R¹ = C₄H₉-n; 1,3-oxathiolan-2-yl-CH₃ | amorphous solid |
| 64 | Cl | H | R¹ = C₄H₉-n; 1,3-dithiolan-2-yl-CH₃ | amorphous solid |
| 65 | Br | H | R¹ = C₄H₉-n; –C(=N–OCH₂C≡CH)–CH₃ | $n_D^{25}$ 1.5343 |
| 66 | Cl | H | R¹ = C₄H₉-n; –C(=N–OC₄H₉-i)–CH₃ | $n_D^{25}$ 1.5437 |
| 67 | Cl | H | R¹ = C₃H₇-n; 1,3-dioxolan-2-yl-CH₃ | mp 68–72° C. |
| 68 | Cl | H | R¹ = C₃H₇-n; –C(=NOH)–CH₃ | amorphous solid |
| 69 | Br | H | R¹ = C₃H₇-n; –C(=NOH)–CH₃ | mp 198–202° C. |
| 70 | Cl | H | R¹ = C₄H₉-n; –C(=NOH)–CH₃ | mp 181–185° C. |
| 71 | Br | H | R¹ = C₄H₉-n; –C(=NOH)–CH₃ | mp 128–131° C. |

The following compounds are also important compounds of the present invention.

N-[2,4-dichloro-5-(cyclopentanon-2-yloxy)phenyl]-3,4,5,6-tetrahydrophthalimide, N-[4-chloro-3-(4-methylcycloopentanon-2-yloxy)phenyl]-3,4,5,6-tetrahydrophthalimide, N-[4-bromo-3-(4-methylcyclopentanon-2-yloxy)phenyl]-3,4,5,6-tetrahydrophthalimide, N-[2,4-dichloro-5-(γ-valerolacton-3-yloxy)phenyl]-3,4,5,6-tetrahydrophthalimide, N-[4-bromo-3-(δ-valerolacton-3-yloxy)phenyl]-3,4,5,6-tetrahydrophthalimide, N-[4-chloro-3-(2,2-dipropoxycyclopentyloxy)phenyl]-3,4,5,6-tetrahydrophthalimide, N-[4-bromo-3-(2,2-dipropoxycyclopentyloxy)phenyl]-3,4,5,6-tetrahydrophthalimide, 4-[4-chloro-3-(2,2-dibutoxycycloopentyloxy)phenyl]-3,4,5,6-tetrahydrophthalimide, N-[4-chloro-(2,2-dimethoxycyclopentyloxy)phenyl]-

3,4,5,6-tetrahydrophthalimide, N-[4-bromo-3-(2,2-dimethoxycyclopentyloxy)phenyl]-3,4,5,6-tetrahydrophthalimide, N-[4-chloro-3-(2,2-trimethylenedioxycyclopentyloxy)phenyl]-3,4,5,6-tetrahydrophthalimide, N-[4-bromo-3-(2,2-trimethylenedioxycyclopentyloxy)phenyl]-3,4,5,6-tetrahydrophthalimide, and N-[2,4-dichloro-5-(2,2-diethoxycyclopentyloxy)phenyl]-3,4,5,6-tetrahydrophthalimide.

Among these compounds of the present invention, the following compounds have especially superior herbicidal activity in upland.

N-[4-chloro-3-(1-ethyl-2-oxopropoxy)phenyl]-3,4,5,6-tetrahydrophthalimide (Compound No. 45), N-[4-chloro-3-(1-methyl-2,2-propylenedioxypropoxy)-phenyl]-3,4,5,6-tetrahydrophthalimide (Compound No. 29) and N-[4-bromo-3-(2,2-diethoxycyclopentyloxy)-phenyl]-3,4,5,6-tetrahydrophthalimide (Compound No. 7).

The compounds (I) can be used as herbicides without an adjuvant. Thus, the compounds (I) are usually used in a form of herbicidal compositions such as an emulsifiable concentrate, a wettable powder, a dust, a granule and a tablet which can be prepared by admixing the active ingredient with a suitable inert liquor or solid carrier and another adjuvant such as suitable surfactants.

Suitable liquid carriers include toluene, xylene, methyl naphthalene, cyclohexane, butanol, glycol, dimethylsulfoxide, dimethylformamide, acetone, methyl isobutyl ketone, animal or vegetable oils, fatty acid, fatty acid esters and water.

Suitable solid carriers include clay, kaolin clay, talc, bentonite, diatomaceous earth, silica, calcium carbonate, soybean powder, wheat powder, other plant powder etc.

It is also possible to incorporate the other agricultural chemical such as agricultural fungicides, insecticides, nematocides, and the other herbicides, plant growth regulators, soil improvers and fertilizers.

It is also possible to incorporate a suitable adjuvant such as a spreader, an emulsifier, a wet spreader and a sticker for improving the herbicidal effect.

Suitable amounts of the active ingredient and the adjuvants in the herbicidal compositions of the present invention are as follows.

| | (% by weight) | | | |
|---|---|---|---|---|
| | Active ingredient | Surfactant | Carrier | Other additive |
| Wettable powder | 5 to 80 | 2 to 20 | 10 to 93 | 0 to 5 |
| Flowable | 5 to 60 | 5 to 30 | 10 to 90 | 0 to 20 |
| Granule | 1 to 20 | 2 to 10 | 70 to 97 | 0 to 5 |
| Emulsifiable concentrate | 5 to 80 | 5 to 30 | 10 to 90 | 0 to 5 |

A dose of the compound (I) as the herbicide is depending upon a kind of the compound, a kind of weed, a season and method of the application and a kind of soil and is usually in a range of 2 to 80 g./are.

The compounds (I) as the herbicide of the present invention can be applied in flooded soil treatment at preemergence or in treatments at growth period, and impart excellent herbicidal activity to annual weeds and perennial weeds and have low phytotoxicity to transplanted rice seedling which are remarkably preferable as herbicide in paddy field. In the soil treatment at preemergence and the foliage and soil treatment in upland, the compounds of the present invention impart excellent herbicidal activity to annual weeds and perennial weeds and high residual effect. Even though it is applied at high concentration. The phytotoxicity to crop plants is remarkably low.

The compounds as a herbicide of the present invention are used for controlling the following weeds.

| Dicotyledonous weeds: | |
|---|---|
| Scientific name | (American name) |
| Ipomoea spp. | (morningglories) |
| Galium aparine | (bedstraw) |
| Stellaria media | (common chickweed) |
| Galinsoga ciliata | (hairy galinsoga) |
| Chenopodium album var. controrubrum | |
| Chenopodium album | (lambsquarters) |
| Abutilon theophrasti | (velvetleaf) |
| Brassica kaber var. pinnatifida | (wild mustard) |
| Capsella bursa-pastoris | (shepherdspurse) |
| Rumex japonicus | |
| Polygonum persicaria | (ladysthumb) |
| Portulaca aleracea | (common purslane) |
| Amaranthus lividus | (livid amaranth) |
| Ambrosia artemisifolia | (common ragweed) |
| Rotala indica | (toothcup) |
| Lindernia procumbens | |
| Eclipta prostrata | |
| Bidens tripartita | |
| Dopatrium junceum | |
| Elatine triandra | |
| Polygonum thunbergii | |

| Monocotyledonous weeds: | |
|---|---|
| Scientific name | (American name) |
| Echinochloa crus(barnyard grass) | |
| Digitaria sanguinalis | (large crabgrass) |
| Eleusine indica | (goosegrass) |
| Setaria viridis | (green foxtail) |
| Poa annua | (annual bluegrass) |
| Alopecurus aequalis | (water foxtail) |
| Cynodon dactylon | (bermudagrass) |
| Agropyron repens | (quackgrass) |
| Cyperus microiria | |
| Cyperus difformis | |
| Eleocharis kuroguwai | (water chestnut) |
| Eleocharis acicularis | (slender spikerush) |
| Scirpus juncoides | (hardstem bulrush) |
| Cyperus serotinus | |
| Scirpus maritimus | |
| Monochoria vaginalis | |
| Sagitaria pygmaea | |
| Alisma canaliculatum | |
| Sagitaria trifolia | |

The compounds as a herbicide of the present invention can be used as selective herbicides in the cultivation of the following crops.

| Dicotyledonous crops: | |
|---|---|
| Glycine max | (soybean) |
| Gossypium indicum | (cotton) |
| Beta vulgaris | (sugar beet) |
| Helianthus annuus | (sunflower) |
| Pisum sativum | (pea) |
| Solanum tuberosum | (potato) |
| Cucumis sativus | (cucumber) |
| Monocotyledonous crops: | |
| Oryza sativa | (rice) |
| Triticum aestivum | (wheat) |
| Hordeum vulgare | (barley) |
| Avena fatua | (oat) |
| Secale cereale | (rye) |
| Zea mays | (corn) |

| -continued | |
|---|---|
| *Saccharum officinarum* | (sugar cane) |

The application of the compounds as a herbicide of the present invention is not only to the aforementioned plants but also to the other plants by the same manner.

The herbicides and herbicidal compositions of the present invention will be further illustrated by certain examples for preparations and herbicidal experimental tests which are provided for purposes of illustration only and are not intended to be limiting the present invention.

In the preparation and the experiments, the term "part" means "part by weight" and Compound numbers correspond to Compounds shown in Table 1. As references, the following compounds are also used.

Reference A:
N-(3-methoxy-4-chlorophenyl)-3,4,5,6-tetrahydrophthalimide

Reference B:
N-(3-methoxy-4-bromophenyl)-3,4,5,6-tetrahydrophthalimide

Reference C:
2,4,6-trichlorophenyl-4'-nitrophenyl ether

Reference D:
S-(2-chlorobenzyl)-N,N-diethylthiol-carbamate

Reference E:
3-(3,4-dichlorophenyl)-1,1-dimethylurea

Reference F:
2,4-dichlorophenyl-4'-nitrophenyl ether

Reference G:
3,4-dichloropropionic anilide

| Wettable powder: | |
|---|---|
| Compound shown in Table 1 | 50 parts |
| Carplex #80 (Shionogi Seiyaku K.K.) | 15 parts |
| N,N—kaolin clay (Tsuchiya Kaolin K.K.) | 30 parts |
| Sorpol 8070 (Toho Kagaku K.K.) (higher alkyl sulfate surfactant) | 5 parts |

The components were uniformly mixed and ground to obtain a wettable powder containing 50% of the active ingredient.

| Granule: | |
|---|---|
| Compound shown in Table 1 | 5 parts |
| Clay (Nippon Talc K.K.) | 38 parts |
| Bentonite (Hojunyoko K.K.) | 55 parts |
| Aerol CT-1 (Toho Kagaku K.K.) (succinate type surfactant) | 2 parts |

The components were mixed with water and kneaded and granulated by a granulating machine and dried at 60° C. for 2 hours to obtain a granule containing 5% of the active ingredient.

| Emulsifiable concentrate: | |
|---|---|
| Compound shown in Table 1 | 30 parts |
| Xylene | 30 parts |
| Dimethylformamide | 25 parts |

The compound was dissolved into the mixed solvent and then, 15 parts of polyoxyethylene type surfactant (Sorpol 3005X: Toho Kagaku K.K.) was admixed to obtain an emulsifiable concentrate containing 30% of the active ingredient.

In the tests, the following weeds were used and the weeds are shown by the following symbols.

Barnyardgrass (*Echinochloa crus-galli*): B.G.
Tooth cup (*Rotala indica*): T.C.
Narrowleaf waterplantain (*Alisma canaliculatum*): N.W.
Hardstem bulrush (*Scirpus juncoides*): H.B.
Crabgrass (*Digitaria songuinalis* (L.) Scop): C.G.
Ladys thumb (*Polygonum persicaria*): L.T.
Lambsguarter (*Chemopoduim album* L.): L.A.
Sawa millet (*Echinochloa frumentacea*): S.M.

Test A:

(i) Flooded paddy field test for preemergence of paddy weeds:

Each pot of 1/2500 are filled with paddy diluvium soil and manured (fertilizer application) and seeds of Barnyardgrass, Tooth cup, Hardstem bulrush, and Narrowleaf waterplantain were sown. The seeds were mixed well in the upper layer having a thickness of 2 cm and the pot was flooded in a depth of about 3 cm. Next day, each wettable powder containing each of Compounds of the present invention and Reference Compounds as the active ingredient was diluted with water nd the diluted solution was applied so as to give each dose (40, 20, 10 or 5 g./are) of the active ingredient by a drop treatment under the flooded surface.

For three days after the treatment, a leaching loss of water was given at a rate of 3 cm/day and the pot was kept in a greenhouse.

Twenty one days after the treatment, survival quantities of the plants were measured to find herbicidal effects to weeds. The results are shown in Table 2. Herbicidal effects are rated by the following equation and ratings.

$$\left(1 - \frac{\text{Survival terrestrial weed weight in treated pot}}{\text{Survival terrestrial weed in non-treated pot}}\right) \times 100 = Y\ (\%)$$

| Herbicidal effect rating | Y (%) |
|---|---|
| 0 | 0–5 |
| 1 | 5–30 |
| 2 | 30–50 |
| 3 | 50–70 |
| 4 | 70–80 |
| 5 | 90–100 |

In tables, "Dose" means "dose of active ingredient" (g/are).

Test B:

In accordance with the experiment of Test A, each test was carried out by using the compounds shown in Table 3. The results are shown in Table 3.

TABLE 2

| Compound No. | Dose of active ingredient (g/a) | Herbicidal Effect | | | |
|---|---|---|---|---|---|
| | | B.G. | T.C. | N.W. | H.B. |
| 1 | 40 | 5 | 5 | 5 | 5 |
| | 20 | 4 | 5 | 4 | 4 |
| | 10 | 4 | 4 | 4 | 3 |
| 2 | 20 | 5 | 5 | 5 | 5 |

TABLE 2-continued

| Compound No. | Dose of active ingredient (g/a) | B.G. | T.C. | N.W. | H.B. |
|---|---|---|---|---|---|
|  | 10 | 5 | 5 | 5 | 4 |
|  | 5 | 4 | 5 | 5 | 4 |
| 3 | 20 | 5 | 5 | 5 | 5 |
|  | 10 | 5 | 5 | 5 | 5 |
|  | 5 | 5 | 5 | 5 | 4 |
| 4 | 40 | 5 | 5 | 5 | 5 |
|  | 20 | 4 | 5 | 5 | 5 |
|  | 10 | 4 | 5 | 5 | 3 |
| 5 | 20 | 5 | 5 | 5 | 5 |
|  | 10 | 5 | 5 | 5 | 5 |
|  | 5 | 5 | 5 | 5 | 5 |
| 6 | 20 | 5 | 5 | 5 | 5 |
|  | 10 | 5 | 5 | 5 | 5 |
|  | 5 | 5 | 5 | 5 | 5 |
| 7 | 20 | 5 | 5 | 5 | 5 |
|  | 10 | 5 | 5 | 5 | 5 |
|  | 5 | 5 | 5 | 5 | 4 |
| 8 | 20 | 5 | 5 | 5 | 5 |
|  | 10 | 5 | 5 | 5 | 5 |
|  | 5 | 5 | 5 | 5 | 5 |
| 9 | 20 | 5 | 5 | 5 | 5 |
|  | 10 | 5 | 5 | 5 | 5 |
|  | 5 | 5 | 5 | 5 | 5 |
| 10 | 20 | 5 | 5 | 5 | 5 |
|  | 10 | 4 | 5 | 5 | 4 |
|  | 5 | 4 | 5 | 5 | 3 |
| 11 | 20 | 5 | 5 | 5 | 5 |
|  | 10 | 5 | 5 | 5 | 5 |
|  | 5 | 4 | 5 | 5 | 4 |
| 12 | 20 | 5 | 5 | 5 | 5 |
|  | 10 | 5 | 5 | 5 | 5 |
|  | 5 | 5 | 5 | 5 | 5 |
| 13 | 20 | 5 | 5 | 5 | 5 |
|  | 10 | 5 | 5 | 5 | 5 |
|  | 5 | 5 | 5 | 5 | 5 |
| Reference A | 40 | 5 | 5 | 5 | 5 |
|  | 20 | 4 | 4 | 4 | 4 |
|  | 10 | 3 | 4 | 3 | 3 |
| Reference C | 20 | 5 | 5 | 3 | 3 |
|  | 10 | 4 | 5 | 2 | 1 |
|  | 5 | 2 | 3 | 0 | 0 |
| Reference D | 40 | 5 | 4 | 2 | 5 |
|  | 20 | 3 | 4 | 0 | 4 |
|  | 10 | 1 | 2 | 0 | 3 |
| Non-treatment | — | 0 | 0 | 0 | 0 |

TABLE 3

| Compound No. | Dose of active ingredient (g/a) | B.G. | T.C. | N.W. | H.B. |
|---|---|---|---|---|---|
| 14 | 20 | 5 | 5 | 5 | 5 |
|  | 10 | 5 | 5 | 5 | 5 |
|  | 5 | 5 | 5 | 5 | 5 |
| 15 | 20 | 5 | 5 | 5 | 5 |
|  | 10 | 5 | 5 | 5 | 5 |
|  | 5 | 5 | 5 | 5 | 5 |
| 16 | 20 | 5 | 5 | 5 | 5 |
|  | 10 | 5 | 5 | 5 | 5 |
|  | 5 | 5 | 5 | 5 | 5 |
| 17 | 20 | 5 | 5 | 5 | 5 |
|  | 10 | 5 | 5 | 5 | 5 |
|  | 5 | 5 | 5 | 5 | 4 |
| 18 | 20 | 5 | 5 | 5 | 5 |
|  | 10 | 5 | 5 | 5 | 5 |
|  | 5 | 5 | 5 | 5 | 5 |
| 19 | 20 | 5 | 5 | 5 | 5 |
|  | 10 | 5 | 5 | 5 | 5 |
|  | 5 | 5 | 5 | 5 | 5 |
| 20 | 20 | 5 | 5 | 5 | 5 |
|  | 10 | 5 | 5 | 5 | 5 |
|  | 5 | 5 | 5 | 5 | 5 |
| 21 | 20 | 5 | 5 | 5 | 5 |
|  | 10 | 5 | 5 | 5 | 5 |
|  | 5 | 5 | 5 | 5 | 5 |

TABLE 3-continued

| Compound No. | Dose of active ingredient (g/a) | B.G. | T.C. | N.W. | H.B. |
|---|---|---|---|---|---|
| 22 | 20 | 5 | 5 | 5 | 5 |
|  | 10 | 5 | 5 | 5 | 5 |
|  | 5 | 5 | 5 | 5 | 5 |
| 23 | 20 | 5 | 5 | 5 | 5 |
|  | 10 | 5 | 5 | 5 | 5 |
|  | 5 | 5 | 5 | 5 | 5 |
| 24 | 20 | 5 | 5 | 5 | 5 |
|  | 10 | 5 | 5 | 5 | 5 |
|  | 5 | 5 | 5 | 5 | 5 |
| 25 | 20 | 5 | 5 | 5 | 5 |
|  | 10 | 5 | 5 | 5 | 5 |
|  | 5 | 5 | 5 | 5 | 5 |
| 26 | 20 | 5 | 5 | 5 | 5 |
|  | 10 | 5 | 5 | 5 | 5 |
|  | 5 | 5 | 5 | 5 | 5 |
| 27 | 20 | 5 | 5 | 5 | 5 |
|  | 10 | 5 | 5 | 5 | 5 |
|  | 5 | 5 | 5 | 5 | 5 |
| 28 | 20 | 5 | 5 | 5 | 5 |
|  | 10 | 5 | 5 | 5 | 5 |
|  | 5 | 5 | 5 | 5 | 5 |
| 29 | 20 | 5 | 5 | 5 | 5 |
|  | 10 | 5 | 5 | 5 | 5 |
|  | 5 | 5 | 5 | 5 | 5 |
| 30 | 20 | 5 | 5 | 5 | 5 |
|  | 10 | 5 | 5 | 5 | 5 |
|  | 5 | 5 | 5 | 5 | 5 |
| 31 | 20 | 5 | 5 | 5 | 5 |
|  | 10 | 5 | 5 | 5 | 5 |
|  | 5 | 5 | 5 | 5 | 5 |
| 32 | 20 | 5 | 5 | 5 | 5 |
|  | 10 | 5 | 5 | 5 | 5 |
|  | 5 | 5 | 5 | 5 | 5 |
| 33 | 20 | 5 | 5 | 5 | 5 |
|  | 10 | 5 | 5 | 5 | 5 |
|  | 5 | 5 | 5 | 5 | 5 |
| 34 | 20 | 5 | 5 | 5 | 5 |
|  | 10 | 5 | 5 | 5 | 5 |
|  | 5 | 5 | 5 | 5 | 4 |
| 35 | 20 | 5 | 5 | 5 | 5 |
|  | 10 | 5 | 5 | 5 | 5 |
|  | 5 | 5 | 5 | 5 | 4 |
| 36 | 20 | 5 | 5 | 5 | 5 |
|  | 10 | 5 | 5 | 5 | 5 |
|  | 5 | 5 | 5 | 5 | 5 |
| 37 | 20 | 5 | 5 | 5 | 5 |
|  | 10 | 5 | 5 | 5 | 5 |
|  | 5 | 5 | 5 | 5 | 5 |
| 38 | 20 | 5 | 5 | 5 | 5 |
|  | 10 | 5 | 5 | 5 | 5 |
|  | 5 | 5 | 5 | 5 | 5 |
| 39 | 20 | 5 | 5 | 5 | 5 |
|  | 10 | 5 | 5 | 5 | 5 |
|  | 5 | 5 | 5 | 5 | 4 |
| 40 | 20 | 5 | 5 | 5 | 5 |
|  | 10 | 5 | 5 | 5 | 5 |
|  | 5 | 5 | 5 | 5 | 5 |
| 41 | 20 | 5 | 5 | 5 | 5 |
|  | 10 | 5 | 5 | 5 | 5 |
|  | 5 | 4 | 5 | 5 | 4 |
| 42 | 20 | 5 | 5 | 5 | 5 |
|  | 10 | 5 | 5 | 5 | 5 |
|  | 5 | 4 | 5 | 5 | 5 |
| 43 | 20 | 5 | 5 | 5 | 5 |
|  | 10 | 5 | 5 | 5 | 5 |
|  | 5 | 5 | 5 | 5 | 5 |
| 44 | 20 | 5 | 5 | 5 | 5 |
|  | 10 | 5 | 5 | 5 | 4 |
|  | 5 | 4 | 5 | 5 | 4 |
| 45 | 20 | 5 | 5 | 5 | 5 |
|  | 10 | 5 | 5 | 5 | 5 |
|  | 5 | 5 | 5 | 5 | 5 |
| 46 | 20 | 5 | 5 | 5 | 5 |
|  | 10 | 5 | 5 | 5 | 5 |
|  | 5 | 5 | 5 | 5 | 5 |
| 47 | 20 | 5 | 5 | 5 | 5 |
|  | 10 | 5 | 5 | 5 | 5 |

TABLE 3-continued

| Compound No. | Dose of active ingredient (g/a) | Herbicidal Effect | | | |
|---|---|---|---|---|---|
| | | B.G. | T.C. | N.W. | H.B. |
| 48 | 5 | 5 | 5 | 5 | 5 |
| | 20 | 5 | 5 | 5 | 5 |
| | 10 | 5 | 5 | 5 | 5 |
| 49 | 5 | 5 | 5 | 5 | 5 |
| | 20 | 5 | 5 | 5 | 5 |
| | 10 | 5 | 5 | 5 | 5 |
| 50 | 5 | 5 | 5 | 5 | 4 |
| | 20 | 5 | 5 | 5 | 5 |
| | 10 | 5 | 5 | 5 | 5 |
| 51 | 5 | 5 | 5 | 5 | 5 |
| | 20 | 5 | 5 | 5 | 5 |
| | 10 | 5 | 5 | 5 | 5 |
| 52 | 5 | 5 | 5 | 5 | 4 |
| | 20 | 5 | 5 | 5 | 5 |
| | 10 | 5 | 5 | 5 | 5 |
| 53 | 5 | 5 | 5 | 5 | 5 |
| | 20 | 5 | 5 | 5 | 5 |
| | 10 | 5 | 5 | 5 | 5 |
| 54 | 5 | 5 | 5 | 5 | 5 |
| | 20 | 5 | 5 | 5 | 5 |
| | 10 | 5 | 5 | 5 | 5 |
| 55 | 5 | 5 | 5 | 5 | 5 |
| | 20 | 5 | 5 | 5 | 5 |
| | 10 | 5 | 5 | 5 | 5 |
| 56 | 5 | 5 | 5 | 5 | 5 |
| | 20 | 5 | 5 | 5 | 5 |
| | 10 | 5 | 5 | 5 | 5 |
| 57 | 5 | 5 | 5 | 5 | 4 |
| | 20 | 5 | 5 | 5 | 5 |
| | 10 | 5 | 5 | 5 | 5 |
| 58 | 5 | 5 | 5 | 5 | 5 |
| | 20 | 5 | 5 | 5 | 5 |
| | 10 | 5 | 5 | 5 | 5 |
| 59 | 5 | 5 | 5 | 5 | 5 |
| | 20 | 5 | 5 | 5 | 5 |
| | 10 | 5 | 5 | 5 | 5 |
| 60 | 5 | 5 | 5 | 5 | 4 |
| | 20 | 5 | 5 | 5 | 5 |
| | 10 | 5 | 5 | 5 | 5 |
| 61 | 5 | 5 | 5 | 5 | 5 |
| | 20 | 5 | 5 | 5 | 5 |
| | 10 | 5 | 5 | 5 | 5 |
| 62 | 5 | 5 | 5 | 5 | 5 |
| | 20 | 5 | 5 | 5 | 5 |
| | 10 | 5 | 5 | 5 | 5 |
| 63 | 5 | 4 | 5 | 5 | 5 |
| | 20 | 5 | 5 | 5 | 5 |
| | 10 | 5 | 5 | 5 | 5 |
| Reference A | 5 | 5 | 5 | 5 | 4 |
| | 40 | 5 | 5 | 5 | 5 |
| | 20 | 4 | 5 | 4 | 4 |
| | 10 | 3 | 3 | 4 | 2 |
| Reference B | 40 | 5 | 5 | 5 | 5 |
| | 20 | 5 | 4 | 5 | 4 |
| | 10 | 3 | 3 | 3 | 3 |
| Reference C | 20 | 5 | 5 | 3 | 4 |
| | 10 | 4 | 5 | 2 | 1 |
| | 5 | 2 | 4 | 0 | 0 |
| Reference D | 40 | 5 | 4 | 2 | 5 |
| | 20 | 4 | 4 | 0 | 4 |
| | 10 | 1 | 2 | 0 | 3 |
| Non-treatment | — | 0 | 0 | 0 | 0 |

Test C:

Phytotoxicity test for rice seedlings:

Each Wagner pot of 1/5,000 was filled with paddy diluvium soil and manured (fertilizer application) and puddled with suitable water and two rice seedlings of 2.6 leaf stage (Sasanishiki, height of 14.3 cm: good seedling) were transplanted in a depth of about 2 cm, and the pot was flooded in a depth of 1.5 cm.

One or seven days after the transplantation, each granule containing each of Compounds of the present invention and Reference Compound was fallen on the flooded surface at each dose (40, 20 or 10 g/are) of the compound.

For three days after the treatment, a leaching loss of water was given at a rate of 3 cm/day and the pot was kept in greenhouse.

Twenty one days after the treatment, phytotoxicities of the compounds to rice seedlings were observed. The results are shown in Table 4.

The phytotoxicites were rated as follows.

$$\left(1 - \frac{\text{Weight of exposed rice seedling in treated pot}}{\text{Weight of exposed rice seedling in non-treated pot}}\right) \times 100 = Y\ (\%)$$

| Rating of phytotoxicity | Y (%) |
|---|---|
| 0 | 0–5 |
| 1 | 5–10 |
| 2 | 10–20 |
| 3 | 20–40 |
| 4 | 40–60 |
| 5 | 60–100 |

Test D:

In accordance with the experiment of Test C, each test was carried out by using the compounds shown in Table 5. The results are shown in Table 5.

TABLE 4

| Compound No. | Dose of active ingredient (g/a) | Phytotoxicity to rice seedling | |
|---|---|---|---|
| | | one day after transplantation | 7 days after transplantation |
| 1 | 40 | 0 | 0 |
| | 20 | 0 | 0 |
| | 10 | 0 | 0 |
| 2 | 40 | 1 | 0 |
| | 20 | 0 | 0 |
| | 10 | 0 | 0 |
| 3 | 40 | 1 | 0 |
| | 20 | 0 | 0 |
| | 10 | 0 | 0 |
| 4 | 40 | 0 | 0 |
| | 20 | 0 | 0 |
| | 10 | 0 | 0 |
| 5 | 40 | 0 | 0 |
| | 20 | 0 | 0 |
| | 10 | 0 | 0 |
| 6 | 40 | 1 | 1 |
| | 20 | 0 | 0 |
| | 10 | 0 | 0 |
| 7 | 40 | 0 | 0 |
| | 20 | 0 | 0 |
| | 10 | 0 | 0 |
| 8 | 40 | 0 | 0 |
| | 20 | 0 | 0 |
| | 10 | 0 | 0 |
| 9 | 40 | 1 | 0 |
| | 20 | 0 | 0 |
| | 10 | 0 | 0 |
| 10 | 40 | 0 | 0 |
| | 20 | 0 | 0 |
| | 10 | 0 | 0 |
| 11 | 40 | 0 | 0 |
| | 20 | 0 | 0 |
| | 10 | 0 | 0 |
| 12 | 40 | 0 | 0 |
| | 20 | 0 | 0 |
| | 10 | 0 | 0 |
| 13 | 40 | 1 | 0 |
| | 20 | 0 | 0 |
| | 10 | 0 | 0 |

TABLE 4-continued

| Compound No. | Dose of active ingredient (g/a) | Phytotoxicity to rice seedling one day after transplantation | 7 days after transplantation |
|---|---|---|---|
| Reference A | 40 | 2 | 2 |
|  | 20 | 0 | 0 |
|  | 10 | 0 | 0 |
| Reference C | 40 | 3 | 2 |
|  | 20 | 2 | 0 |
|  | 10 | 0 | 0 |
| Reference D | 40 | 4 | 2 |
|  | 20 | 2 | 1 |
|  | 10 | 0 | 0 |
| Non-treatment | — | 0 | 0 |

TABLE 5

| Compound No. | Dose of active ingredient (g/a) | Phytotoxicity to rice seedling one day after transplantation | 7 days after transplantation |
|---|---|---|---|
| 23 | 40 | 2 | 1 |
|  | 20 | 0 | 0 |
|  | 10 | 0 | 0 |
| 24 | 40 | 1 | 0 |
|  | 20 | 0 | 0 |
|  | 10 | 0 | 0 |
| 25 | 40 | 1 | 0 |
|  | 20 | 0 | 0 |
|  | 10 | 0 | 0 |
| 26 | 40 | 1 | 1 |
|  | 20 | 0 | 0 |
|  | 10 | 0 | 0 |
| 27 | 40 | 1 | 1 |
|  | 20 | 0 | 0 |
|  | 10 | 0 | 0 |
| 28 | 40 | 1 | 0 |
|  | 20 | 0 | 0 |
|  | 10 | 0 | 0 |
| 29 | 40 | 0 | 0 |
|  | 20 | 0 | 0 |
|  | 10 | 0 | 0 |
| 30 | 40 | 1 | 0 |
|  | 20 | 0 | 0 |
|  | 10 | 0 | 0 |
| 31 | 40 | 2 | 0 |
|  | 20 | 0 | 0 |
|  | 10 | 0 | 0 |
| 32 | 40 | 0 | 0 |
|  | 20 | 0 | 0 |
|  | 10 | 0 | 0 |
| 33 | 40 | 1 | 0 |
|  | 20 | 0 | 0 |
|  | 10 | 0 | 0 |
| 34 | 40 | 0 | 0 |
|  | 20 | 0 | 0 |
|  | 10 | 0 | 0 |
| 35 | 40 | 1 | 1 |
|  | 20 | 0 | 0 |
|  | 10 | 0 | 0 |
| 36 | 40 | 0 | 0 |
|  | 20 | 0 | 0 |
|  | 10 | 0 | 0 |
| 37 | 40 | 0 | 0 |
|  | 20 | 0 | 0 |
|  | 10 | 0 | 0 |
| 38 | 40 | 2 | 1 |
|  | 20 | 0 | 0 |
|  | 10 | 0 | 0 |
| 39 | 40 | 0 | 0 |
|  | 20 | 0 | 0 |
|  | 10 | 0 | 0 |
| 40 | 40 | 1 | 0 |
|  | 20 | 0 | 0 |
|  | 10 | 0 | 0 |
| 41 | 40 | 1 | 1 |
|  | 20 | 0 | 0 |
|  | 10 | 0 | 0 |
| 42 | 40 | 0 | 0 |
|  | 20 | 0 | 0 |
|  | 10 | 0 | 0 |
| 43 | 40 | 0 | 0 |
|  | 20 | 0 | 0 |
|  | 10 | 0 | 0 |
| 44 | 40 | 1 | 0 |
|  | 20 | 0 | 0 |
|  | 10 | 0 | 0 |
| 45 | 40 | 0 | 0 |
|  | 20 | 0 | 0 |
|  | 10 | 0 | 0 |
| 46 | 40 | 1 | 0 |
|  | 20 | 0 | 0 |
|  | 10 | 0 | 0 |
| 48 | 40 | 0 | 0 |
|  | 20 | 0 | 0 |
|  | 10 | 0 | 0 |
| 49 | 40 | 2 | 1 |
|  | 20 | 0 | 0 |
|  | 10 | 0 | 0 |
| 50 | 40 | 0 | 1 |
|  | 20 | 0 | 0 |
|  | 10 | 0 | 0 |
| 51 | 40 | 0 | 0 |
|  | 20 | 0 | 0 |
|  | 10 | 0 | 0 |
| 52 | 40 | 0 | 0 |
|  | 20 | 0 | 0 |
|  | 10 | 0 | 0 |
| 53 | 40 | 1 | 1 |
|  | 20 | 0 | 0 |
|  | 10 | 0 | 0 |
| 54 | 40 | 1 | 0 |
|  | 20 | 0 | 0 |
|  | 10 | 0 | 0 |
| 55 | 40 | 0 | 0 |
|  | 20 | 0 | 0 |
|  | 10 | 0 | 0 |
| 56 | 40 | 1 | 0 |
|  | 20 | 0 | 0 |
|  | 10 | 0 | 0 |
| 57 | 40 | 2 | 1 |
|  | 20 | 0 | 0 |
|  | 10 | 0 | 0 |
| 58 | 40 | 1 | 1 |
|  | 20 | 0 | 0 |
|  | 10 | 0 | 0 |
| 59 | 40 | 0 | 0 |
|  | 20 | 0 | 0 |
|  | 10 | 0 | 0 |
| 60 | 40 | 0 | 0 |
|  | 20 | 0 | 0 |
|  | 10 | 0 | 0 |
| 61 | 40 | 0 | 0 |
|  | 20 | 0 | 0 |
|  | 10 | 0 | 0 |
| 62 | 40 | 2 | 1 |
|  | 20 | 0 | 0 |
|  | 10 | 0 | 0 |
| 63 | 40 | 0 | 0 |
|  | 20 | 0 | 0 |
|  | 10 | 0 | 0 |
| 64 | 40 | 0 | 0 |
|  | 20 | 0 | 0 |
|  | 10 | 0 | 0 |
| 65 | 40 | 1 | 0 |
|  | 20 | 0 | 0 |
|  | 10 | 0 | 0 |
| 66 | 40 | 1 | 0 |
|  | 20 | 0 | 0 |
|  | 10 | 0 | 0 |
| Reference A | 40 | 2 | 1 |
|  | 20 | 0 | 0 |
|  | 10 | 0 | 0 |
| Reference B | 40 | 2 | 1 |
|  | 20 | 1 | 0 |
|  | 10 | 0 | 0 |
| Reference C | 40 | 3 | 2 |

TABLE 5-continued

| Compound No. | Dose of active ingredient (g/a) | Phytotoxicity to rice seedling one day after transplantation | 7 days after transplantation |
|---|---|---|---|
| | 20 | 2 | 0 |
| | 10 | 0 | 0 |
| Reference D | 40 | 4 | 2 |
| | 20 | 2 | 1 |
| | 10 | 0 | 0 |
| Non-treatment | — | 0 | 0 |

Test E:

Up-land soil treatment test:

Each plastic pot of 1/2,500 are was filled with black volcano ash soil and manured and seeds of wheat, corn, soybean, and cotton were sown and were covered with the soil in a depth of 2 to 3 cm and seeds of weeds of Large crabgrass, Ladys thumb and Lambsquarter were mixed in the covered soil layer. Each wettable powder containing each of Compounds of the present invention and Reference Compound was diluted with water and the solution was sprayed uniformly on the surface of the soil at a dose (40, 20 or 10 g/are) of the compound by a small size power pressurized spray.

Twenty days after the treatment, herbicidal effects were observed and phytotoxicities to the crop plants were also observed. The results are shown in Table 6.

The herbicidal effects are rated as those of Test A and the phytotoxicities to crop plants are rated as those of Test C.

Test F:

In accordance with the experiment of Test E, each test was carried out by using the compounds shown in Table 7. The results are shown in Table 7.

TABLE 6

| Comp. No. | Dose of Comp. (g/a) | Herbicidal effect | | | Phytotoxicity to corn plants | | | |
|---|---|---|---|---|---|---|---|---|
| | | C.G. | L.T. | L.A. | Wheat | Corn | Soy-bean | Cot-ton |
| 1 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 2 | 40 | 4 | 5 | 5 | 0 | 0 | 0 | 0 |
| | 20 | 4 | 5 | 5 | 0 | 0 | 0 | 0 |
| | 10 | 3 | 5 | 5 | 0 | 0 | 0 | 0 |
| 3 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 4 | 40 | 5 | 5 | 5 | 1 | 0 | 0 | 0 |
| | 20 | 5 | 5 | 5 | 0 | 0 | 0 | 0 |
| | 10 | 4 | 5 | 5 | 0 | 0 | 0 | 0 |
| 5 | 40 | 5 | 5 | 5 | 1 | 0 | 0 | 1 |
| | 20 | 5 | 5 | 5 | 0 | 0 | 0 | 0 |
| | 10 | 5 | 5 | 5 | 0 | 0 | 0 | 0 |
| 6 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 7 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 8 | 40 | 5 | 5 | 5 | 1 | 0 | 0 | 0 |
| | 20 | 5 | 5 | 5 | 0 | 0 | 0 | 0 |
| | 10 | 5 | 4 | 5 | 0 | 0 | 0 | 0 |
| 9 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 10 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 11 | 40 | 4 | 5 | 5 | 0 | 0 | 0 | 0 |

TABLE 6-continued

| Comp. No. | Dose of Comp. (g/a) | Herbicidal effect | | | Phytotoxicity to corn plants | | | |
|---|---|---|---|---|---|---|---|---|
| | | C.G. | L.T. | L.A. | Wheat | Corn | Soy-bean | Cot-ton |
| | 20 | 4 | 5 | 5 | 0 | 0 | 0 | 0 |
| | 10 | 4 | 4 | 5 | 0 | 0 | 0 | 0 |
| 12 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 13 | 40 | 5 | 5 | 5 | 1 | 0 | 0 | 0 |
| | 20 | 5 | 5 | 5 | 0 | 0 | 0 | 0 |
| | 10 | 4 | 5 | 5 | 0 | 0 | 0 | 0 |
| Reference A | 40 | 5 | 5 | 5 | 2 | 0 | 0 | 0 |
| | 20 | 4 | 4 | 5 | 0 | 0 | 0 | 0 |
| | 10 | 3 | 2 | 4 | 0 | 0 | 0 | 0 |
| Reference B | 40 | 5 | 5 | 5 | 1 | 0 | 0 | 0 |
| | 20 | 4 | 4 | 4 | 0 | 0 | 0 | 0 |
| | 10 | 3 | 3 | 4 | 0 | 0 | 0 | 0 |
| Reference E | 40 | 5 | 5 | 5 | 4 | 3 | 1 | 2 |
| | 20 | 5 | 5 | 5 | 2 | 1 | 0 | 1 |
| | 10 | 3 | 4 | 4 | 0 | 0 | 0 | 0 |
| Reference F | 40 | 5 | 5 | 5 | 3 | 1 | 1 | 2 |
| | 20 | 4 | 4 | 4 | 2 | 1 | 0 | 0 |
| | 10 | 2 | 3 | 4 | 0 | 0 | 0 | 0 |
| Non-treatment | — | 0 | 0 | 0 | 0 | 0 | 0 | 0 |

TABLE 7

| Comp. No. | Dose of Comp. (g/a) | Herbicidal effect | | | Phytotoxicity to crop plants | | | |
|---|---|---|---|---|---|---|---|---|
| | | C.G. | L.T. | L.A. | Wheat | Corn | Soy-bean | Cot-ton |
| 14 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 15 | 40 | 5 | 5 | 5 | 1 | 0 | 0 | 0 |
| | 20 | 5 | 5 | 5 | 0 | 0 | 0 | 0 |
| | 10 | 5 | 5 | 5 | 0 | 0 | 0 | 0 |
| 16 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 17 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 18 | 40 | 5 | 5 | 5 | 1 | 0 | 0 | 0 |
| | 20 | 5 | 5 | 5 | 0 | 0 | 0 | 0 |
| | 10 | 4 | 5 | 5 | 0 | 0 | 0 | 0 |
| 19 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 20 | 40 | 5 | 5 | 5 | 0 | 0 | 0 | 0 |
| | 20 | 5 | 5 | 5 | 0 | 0 | 0 | 0 |
| | 10 | 3 | 5 | 5 | 0 | 0 | 0 | 0 |
| 21 | 40 | 5 | 5 | 5 | 1 | 0 | 0 | 1 |
| | 20 | 5 | 5 | 5 | 0 | 0 | 0 | 0 |
| | 10 | 5 | 5 | 5 | 0 | 0 | 0 | 0 |
| 22 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 23 | 40 | 5 | 5 | 5 | 1 | 0 | 0 | 0 |
| | 20 | 5 | 5 | 5 | 0 | 0 | 0 | 0 |
| | 10 | 5 | 5 | 5 | 0 | 0 | 0 | 0 |
| 24 | 40 | 5 | 5 | 5 | 1 | 0 | 0 | 0 |
| | 20 | 5 | 5 | 5 | 0 | 0 | 0 | 0 |
| | 10 | 5 | 5 | 5 | 0 | 0 | 0 | 0 |
| 25 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 26 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 27 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 28 | 40 | 5 | 5 | 5 | 1 | 0 | 0 | 0 |
| | 20 | 5 | 5 | 5 | 0 | 0 | 0 | 0 |
| | 10 | 4 | 5 | 5 | 0 | 0 | 0 | 0 |

TABLE 7-continued

| Comp. No. | Dose of Comp. (g/a) | Herbicidal effect | | | Phytotoxicity to crop plants | | | |
|---|---|---|---|---|---|---|---|---|
| | | C.G. | L.T. | L.A. | Wheat | Corn | Soybean | Cotton |
| 29 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 30 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 31 | 40 | 5 | 5 | 5 | 2 | 0 | 0 | 1 |
| | 20 | 5 | 5 | 5 | 0 | 0 | 0 | 0 |
| | 10 | 5 | 5 | 5 | 0 | 0 | 0 | 0 |
| 32 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 33 | 40 | 5 | 5 | 5 | 1 | 0 | 0 | 0 |
| | 20 | 5 | 5 | 5 | 0 | 0 | 0 | 0 |
| | 10 | 5 | 5 | 5 | 0 | 0 | 0 | 0 |
| 34 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 35 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 36 | 40 | 5 | 5 | 5 | 1 | 0 | 0 | 1 |
| | 20 | 5 | 5 | 5 | 0 | 0 | 0 | 0 |
| | 10 | 5 | 5 | 5 | 0 | 0 | 0 | 0 |
| 37 | 40 | 5 | 5 | 5 | 1 | 0 | 0 | 0 |
| | 20 | 5 | 5 | 5 | 0 | 0 | 0 | 0 |
| | 10 | 4 | 5 | 5 | 0 | 0 | 0 | 0 |
| 38 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 39 | 40 | 5 | 5 | 5 | 0 | 0 | 0 | 0 |
| | 20 | 4 | 5 | 5 | 0 | 0 | 0 | 0 |
| | 10 | 3 | 5 | 5 | 0 | 0 | 0 | 0 |
| 40 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 41 | 40 | 4 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 42 | 40 | 5 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 43 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 44 | 40 | 5 | 5 | 5 | 0 | 0 | 0 | 0 |
| | 20 | 5 | 5 | 5 | 0 | 0 | 0 | 0 |
| | 10 | 3 | 4 | 5 | 0 | 0 | 0 | 9 |
| 45 | 40 | 5 | 5 | 5 | 1 | 0 | 0 | 1 |
| | 20 | 5 | 5 | 5 | 0 | 0 | 0 | 0 |
| | 10 | 5 | 5 | 5 | 0 | 0 | 0 | 0 |
| 46 | 40 | 5 | 5 | 5 | 1 | 0 | 0 | 0 |
| | 20 | 5 | 5 | 5 | 0 | 0 | 0 | 0 |
| | 10 | 5 | 5 | 5 | 0 | 0 | 0 | 0 |
| 47 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 48 | 40 | 5 | 5 | 5 | 0 | 0 | 0 | 0 |
| | 20 | 5 | 5 | 5 | 0 | 0 | 0 | 0 |
| | 10 | 4 | 5 | 5 | 2 | 0 | 0 | 0 |
| Reference A | 40 | 5 | 5 | 5 | 2 | 0 | 0 | 0 |
| | 20 | 4 | 4 | 5 | 1 | 0 | 0 | 0 |
| | 10 | 3 | 4 | 3 | 0 | 0 | 0 | 0 |
| Reference B | 40 | 5 | 5 | 5 | 2 | 0 | 0 | 1 |
| | 20 | 4 | 4 | 5 | 1 | 0 | 0 | 0 |
| | 10 | 3 | 3 | 4 | 0 | 0 | 0 | 0 |
| Reference E | 40 | 5 | 5 | 5 | 4 | 3 | 1 | 2 |
| | 20 | 5 | 5 | 5 | 2 | 2 | 0 | 0 |
| | 10 | 3 | 3 | 4 | 0 | 0 | 0 | 0 |
| Reference F | 40 | 5 | 5 | 5 | 3 | 1 | 1 | 1 |
| | 20 | 4 | 4 | 5 | 1 | 1 | 0 | 0 |
| | 10 | 2 | 3 | 4 | 0 | 0 | 0 | 0 |
| Non-treatment | — | 0 | 0 | 0 | 0 | 0 | 0 | 0 |

Test G:

Foliage treatment test:

Each polyethylene pot was filled with black volcano ash soil and manured and seeds of Sawa millet, Large crabgrass and Radish were respectively sown in each pot. The pot was kept in a greenhouse. When Sawa millet and Large crabgrass were grown to 2 leaf stage and Radish to 1 leaf stage, each solution prepared by diluting each emulsifiable concentrate containing each of Compounds of the present invention and Reference Compounds, at a concentration of 0.5, 0.25 or 0.125%, was sprayed at a rate of 10 liter per are by a small power pressurized sprayer and the pot in the greenhouse was observed.

Fifteen days after the treatment, herbicidal effects were observed. The results are shown in Table 8.

The herbicidal effects are rated as those of Test A.

Test H:

In accordance with the experiment of Test G, each herbicidal effect of each of Compounds of the present invention and Reference Compounds was tested. The results are shown in Table 9.

TABLE 8

| Compound No. | Concentration % | Herbicidal effect | | |
|---|---|---|---|---|
| | | S.M. | C.G. | Radish |
| 1 | 0.5 | 4 | 5 | 5 |
| | 0.25 | 4 | 4 | 5 |
| | 0.125 | 3 | 4 | 5 |
| 2 | 0.5 | 5 | 5 | 5 |
| | 0.25 | 4 | 5 | 5 |
| | 0.125 | 3 | 4 | 5 |
| 3 | 0.5 | 5 | 5 | 5 |
| | 0.25 | 5 | 5 | 5 |
| | 0.125 | 5 | 5 | 5 |
| 4 | 0.5 | 4 | 5 | 5 |
| | 0.25 | 4 | 4 | 5 |
| | 0.125 | 4 | 4 | 5 |
| 5 | 0.5 | 5 | 5 | 5 |
| | 0.25 | 4 | 4 | 5 |
| | 0.125 | 4 | 4 | 5 |
| 6 | 0.5 | 5 | 5 | 5 |
| | 0.25 | 4 | 5 | 5 |
| | 0.125 | 4 | 4 | 5 |
| 7 | 0.5 | 5 | 5 | 5 |
| | 0.25 | 5 | 5 | 5 |
| | 0.125 | 4 | 5 | 5 |
| 8 | 0.5 | 5 | 5 | 5 |
| | 0.25 | 5 | 5 | 5 |
| | 0.125 | 5 | 5 | 5 |
| 9 | 0.5 | 5 | 5 | 5 |
| | 0.25 | 4 | 5 | 5 |
| | 0.125 | 4 | 5 | 5 |
| 10 | 0.5 | 5 | 5 | 5 |
| | 0.25 | 4 | 5 | 5 |
| | 0.125 | 3 | 4 | 5 |
| 11 | 0.5 | 5 | 5 | 5 |
| | 0.25 | 4 | 5 | 5 |
| | 0.125 | 4 | 5 | 5 |
| 12 | 0.5 | 5 | 5 | 5 |
| | 0.25 | 4 | 5 | 5 |
| | 0.125 | 4 | 4 | 5 |
| 13 | 0.5 | 5 | 5 | 5 |
| | 0.25 | 4 | 5 | 5 |
| | 0.125 | 4 | 4 | 5 |
| Reference A | 0.5 | 5 | 5 | 5 |
| | 0.25 | 4 | 4 | 5 |
| | 0.125 | 2 | 3 | 2 |
| Reference B | 0.5 | 5 | 5 | 5 |
| | 0.25 | 3 | 4 | 4 |
| | 0.125 | 2 | 3 | 3 |
| Reference G | 0.5 | 5 | 5 | 4 |
| | 0.25 | 4 | 5 | 3 |
| | 0.125 | 3 | 3 | 3 |

TABLE 8-continued

| Compound No. | Concentration % | Herbicidal effect S.M. | C.G. | Radish |
|---|---|---|---|---|
| Non-treatment | — | 0 | 0 | 0 |

TABLE 9

| Compound No. | Concentration % | Herbicidal effect S.M. | C.G. | Radish |
|---|---|---|---|---|
| 14 | 0.5 | 5 | 5 | 5 |
|  | 0.25 | 4 | 5 | 5 |
|  | 0.125 | 4 | 4 | 5 |
| 15 | 0.5 | 5 | 5 | 5 |
|  | 0.25 | 5 | 5 | 5 |
|  | 0.125 | 4 | 5 | 5 |
| 16 | 0.5 | 5 | 5 | 5 |
|  | 0.25 | 5 | 5 | 5 |
|  | 0.125 | 4 | 4 | 5 |
| 17 | 0.5 | 4 | 5 | 5 |
|  | 0.25 | 4 | 5 | 5 |
|  | 0.125 | 4 | 4 | 5 |
| 18 | 0.5 | 5 | 5 | 5 |
|  | 0.25 | 4 | 5 | 5 |
|  | 0.125 | 4 | 5 | 5 |
| 19 | 0.5 | 5 | 5 | 5 |
|  | 0.25 | 5 | 5 | 5 |
|  | 0.125 | 4 | 4 | 5 |
| 20 | 0.5 | 5 | 5 | 5 |
|  | 0.25 | 5 | 5 | 5 |
|  | 0.125 | 4 | 4 | 5 |
| 21 | 0.5 | 5 | 5 | 5 |
|  | 0.25 | 5 | 5 | 5 |
|  | 0.125 | 5 | 5 | 5 |
| 22 | 0.5 | 5 | 5 | 5 |
|  | 0.25 | 5 | 5 | 5 |
|  | 0.125 | 4 | 5 | 5 |
| 23 | 0.5 | 5 | 5 | 5 |
|  | 0.25 | 4 | 5 | 5 |
|  | 0.125 | 4 | 4 | 5 |
| 24 | 0.5 | 5 | 5 | 5 |
|  | 0.25 | 5 | 5 | 5 |
|  | 0.125 | 4 | 5 | 5 |
| 25 | 0.5 | 5 | 5 | 5 |
|  | 0.25 | 5 | 5 | 5 |
|  | 0.125 | 4 | 4 | 5 |
| 26 | 0.5 | 5 | 5 | 5 |
|  | 0.25 | 4 | 5 | 5 |
|  | 0.125 | 4 | 4 | 5 |
| 27 | 0.5 | 4 | 5 | 5 |
|  | 0.25 | 4 | 5 | 5 |
|  | 0.125 | 4 | 4 | 5 |
| 28 | 0.5 | 5 | 5 | 5 |
|  | 0.25 | 4 | 5 | 5 |
|  | 0.125 | 4 | 5 | 5 |
| 33 | 0.5 | 5 | 5 | 5 |
|  | 0.25 | 4 | 5 | 5 |
|  | 0.125 | 4 | 4 | 5 |
| 34 | 0.5 | 5 | 5 | 5 |
|  | 0.25 | 5 | 5 | 5 |
|  | 0.125 | 4 | 4 | 5 |
| 35 | 0.5 | 5 | 5 | 5 |
|  | 0.25 | 5 | 5 | 5 |
|  | 0.125 | 3 | 3 | 5 |
| 36 | 0.5 | 5 | 5 | 5 |
|  | 0.25 | 4 | 5 | 5 |
|  | 0.125 | 4 | 4 | 5 |
| 37 | 0.5 | 5 | 5 | 5 |
|  | 0.25 | 5 | 5 | 5 |
|  | 0.125 | 3 | 4 | 5 |
| 38 | 0.5 | 5 | 5 | 5 |
|  | 0.25 | 4 | 5 | 5 |
|  | 0.125 | 4 | 5 | 5 |
| 39 | 0.5 | 4 | 5 | 5 |
|  | 0.25 | 4 | 5 | 5 |
|  | 0.125 | 3 | 4 | 5 |
| 40 | 0.5 | 5 | 5 | 5 |
|  | 0.25 | 4 | 5 | 5 |
|  | 0.125 | 3 | 3 | 5 |
| 41 | 0.5 | 5 | 5 | 5 |
|  | 0.25 | 4 | 5 | 5 |
|  | 0.125 | 3 | 3 | 5 |
| 42 | 0.5 | 4 | 5 | 5 |
|  | 0.25 | 4 | 4 | 5 |
|  | 0.125 | 4 | 4 | 5 |
| 43 | 0.5 | 5 | 5 | 5 |
|  | 0.25 | 4 | 4 | 5 |
|  | 0.125 | 4 | 4 | 5 |
| 44 | 0.5 | 5 | 5 | 5 |
|  | 0.25 | 4 | 4 | 5 |
|  | 0.125 | 3 | 4 | 5 |
| 45 | 0.5 | 5 | 5 | 5 |
|  | 0.25 | 5 | 5 | 5 |
|  | 0.125 | 5 | 5 | 5 |
| 46 | 0.5 | 5 | 5 | 5 |
|  | 0.25 | 5 | 5 | 5 |
|  | 0.125 | 4 | 5 | 5 |
| 48 | 0.5 | 5 | 5 | 5 |
|  | 0.25 | 4 | 5 | 5 |
|  | 0.125 | 4 | 4 | 5 |
| 49 | 0.5 | 5 | 5 | 5 |
|  | 0.25 | 4 | 5 | 5 |
|  | 0.125 | 4 | 4 | 5 |
| 63 | 0.5 | 5 | 5 | 5 |
|  | 0.25 | 4 | 5 | 5 |
|  | 0.125 | 4 | 4 | 5 |
| 64 | 0.5 | 5 | 5 | 5 |
|  | 0.25 | 4 | 5 | 5 |
|  | 0.125 | 4 | 4 | 5 |
| 65 | 0.5 | 5 | 5 | 5 |
|  | 0.25 | 5 | 5 | 5 |
|  | 0.125 | 3 | 4 | 5 |
| 66 | 0.5 | 5 | 5 | 5 |
|  | 0.25 | 4 | 5 | 5 |
|  | 0.125 | 4 | 4 | 5 |
| 67 | 0.5 | 5 | 5 | 5 |
|  | 0.25 | 4 | 4 | 5 |
|  | 0.125 | 4 | 5 | 5 |
| 68 | 0.5 | 5 | 5 | 5 |
|  | 0.25 | 4 | 5 | 5 |
|  | 0.125 | 4 | 4 | 5 |
| 69 | 0.5 | 5 | 5 | 5 |
|  | 0.25 | 5 | 5 | 5 |
|  | 0.125 | 3 | 4 | 5 |
| 70 | 0.5 | 5 | 5 | 5 |
|  | 0.25 | 5 | 5 | 5 |
|  | 0.125 | 4 | 4 | 5 |
| 71 | 0.5 | 5 | 5 | 5 |
|  | 0.25 | 4 | 5 | 5 |
|  | 0.125 | 4 | 4 | 5 |
| Reference A | 0.5 | 5 | 5 | 5 |
|  | 0.25 | 4 | 4 | 5 |
|  | 0.125 | 2 | 3 | 3 |
| Reference B | 0.5 | 5 | 5 | 5 |
|  | 0.25 | 3 | 4 | 4 |
|  | 0.125 | 2 | 3 | 3 |
| Reference G | 0.5 | 5 | 5 | 4 |
|  | 0.25 | 5 | 5 | 4 |
|  | 0.125 | 2 | 3 | 3 |
| Non-treatment | — | 0 | 0 | 0 |

We claim:

1. A 3,4,5,6-tetrahydrophthalimide of the formula:

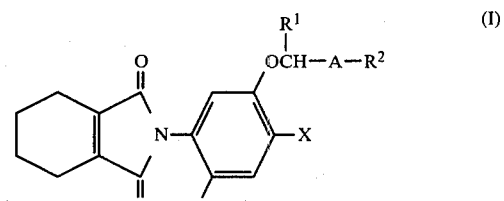

wherein X represents hydrogen or halogen; Y represents hydrogen or halogen; $R^1$ represents hydrogen or a $C_{1-8}$ alkyl group; $R^2$ represents hydrogen or a $C_{1-4}$ alkyl or phenyl group or $R^1$ and $R^2$, when bonded directly together, complete a cyclic radical with the $R^1$ bonded $R^2$ portion of the cyclic radical being a radical of the formula:

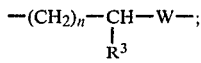

$R^3$ represents hydrogen or a lower alkyl group; W represents —O— or —$CH_2$—; n is 1 or 2, A represents

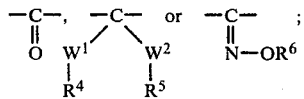

$W^1$ and $W^2$ each represents —O— or —S—; $R^4$ and $R^5$ may be the same or different and each represents a $C_{1-4}$ alkyl group or $R^4$ and $R^5$ when bonded directly together complete a lower alkylene group; $R^6$ represents hydrogen, a $C_{1-6}$ alkyl, a lower alkenyl, a lower alkynyl, a carboxyl-acyl, a $C_{2-5}$ alkoxycarbonyl, carbamoyl, methylcarbamoyl, dimethylcarbamoyl, ethylcarbamoyl, diethylcarbamoyl, butylmethylcarbamoyl, ethylbutylcarbamoyl or a phenylcarbamoyl group.

2. The compound (I) according to claim 1 wherein X represents Cl or Br and Y represents H.

3. The compound (I) according to claim 1, wherein $R^1$ and $R^2$, when bonded directly together, complete a cyclic radical with the $R^1$ bonded $R^2$ portion of the cyclic radical being a radical of the formula:

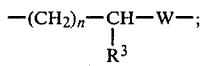

$R^3$ is hydrogen or lower alkyl; W is —O— or —$CH_2$—; n is 1 or 2; A represents

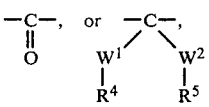

wherein $W^1$ and $W^2$ each represents —O— or —S—; and $R^4$ and $R^5$ can be the same or different and each represents a $C_{1-4}$ alkyl group or $R^4$ and $R^5$, when bonded directly together, complete a —$CH_2CH_2$—, —$CH_2$—$CH_2$—$CH_2$—, or

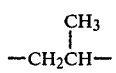

group.

4. The compound (I) according to claim 1 or 2, wherein $R^1$ is H or a $C_{1-8}$ alkyl group; $R^2$ represents H, a $C_{1-4}$ alkyl or phenyl group; A represents —CO—,

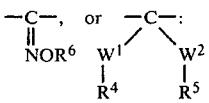

$R^6$ represents H, a $C_{1-6}$ alkyl, allyl, propargyl, a carboxyl-acyl, a $C_{2-5}$ alkoxycarbonyl, carbamoyl, methylcarbamoyl, dimethylcarbamoyl, ethylcarbamoyl, diethylcarbamoyl, butylmethylcarbamoyl, ethylbutylcarbamoyl or a phenylcarbamoyl group; $W^1$ and $W^2$ each represents —O— or —S—; $R^4$ and $R^5$ can be the same or different and each represents $C_{1-4}$ alkyl or $R^4$ and $R^5$ when bonded directly together complete a —$CH_2CH_2$—, —$CH_2$—$CH_2$—$CH_2$—, or

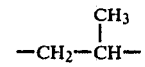

group.

5. The compound (I) according to claim 4 wherein X represents Cl, Y represents H, $R^1$ represents a $C_{1-4}$ alkyl group; $R^2$ represents a $C_{1-4}$ alkyl group; and A represents —CO— group.

6. The compound (I) according to claim 5 wherein X represents Cl; Y represents H; $R^1$ represents an ethyl group; $R^2$ represents a methyl group; and A represents —CO—.

7. The compound (I) according to claim 4, wherein X represents Cl, Y represents H; $R^1$ represents a $C_{1-4}$ alkyl group; $R^2$ represents a $C_{1-4}$ alkyl group; A represents

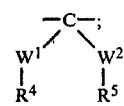

$W^1$ and $W^2$ each represent —O—; $R^4$ and $R^5$ each represent a $C_{1-4}$ alkyl group or, when bonded directly together, complete a —$CH_2CH_2$—, —$CH_2CH_2CH_2$— or

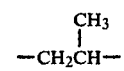

group.

8. The compound (I) according to claim 3, wherein X is Br; Y is H; $R^1$ and $R^2$, when bonded directly togehter, complete a cyclic radical with the $R^1$ bonded $R^2$ portion of the cyclic radical being —$CH_2$—$CH_2$—$CH_2$—; and A represents

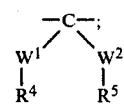

$W^1$ and $W^2$ each represents —O— and $R^4$ and $R^5$ each represents a $C_{1-4}$ alkyl group.

9. A herbicidal composition, which comprises: a herbicidally effective amount of compound (I) of claim 1 as an active ingredient and a carrier.

10. The herbicidal composition according to claim 9 wherein X represents Cl or Br and Y represents H.

11. The herbicidal composition according to claim 9, wherein $R^1$ and $R^2$, when bonded directly together, complete a cyclic radical with the $R^1$ bonded $R^2$ portion of the cyclic radical being a radical of the formula:

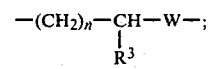

$R^3$ is hydrogen or a lower alkyl group; W is —O— or —CH$_2$—; n is 1 or 2; A represents

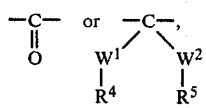

wherein $W^1$ and $W^2$ each represents —O—; and $R^4$ and $R^5$ can be the same or different and each represents a C$_{1-4}$ alkyl group or $R^4$ and $R^5$, when bonded directly together, complete a —CH$_2$—CH$_2$—, —CH$_2$CH$_2$CH$_2$— or

group.

12. The herbicidal composition according to claim 9 or 10, wherein $R^1$ represents H or an alkyl group; $R^2$ represents H, an alkyl or phenyl group; A represents —CO—,

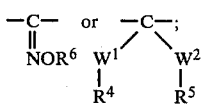

$R^6$ represents H, a C$_{1-6}$ alkyl, a lower alkenyl, a lower alkynyl, carboxyl-acyl, a C$_{2-5}$ alkoxycarbonyl, carbamoyl, methylcarbamoyl, dimethylcarbamoyl, ethylcarbamoyl, diethylcarbamoyl, butylmethylcarbamoyl, ethylbutylcarbamoyl, or a phenylcarbamoyl group; $W^1$ and $W^2$ each represent —O— or —S—; $R^4$ and $R^5$ can be the same or different and each represents a C$_{1-4}$ alkyl group or $R^4$ and $R^5$, when bonded directly together, complete a cyclic radical with the $R^1$ bonded $R^2$ portion of the cyclic radical being a —CH$_2$CH$_2$—, —CH$_2$CH$_2$CH$_2$—, or

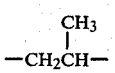

group.

13. The herbicidal composition according to claim 12, wherein X represents Cl, Y represents H; $R^1$ represents a C$_{1-4}$ alkyl group; $R^2$ represents a C$_{1-4}$ alkyl group; A represents —CO— or

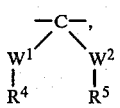

wherein $W^1$ and $W^2$ each represents —O—; $R^4$ and $R^5$ each represents a C$_{1-4}$ alkyl group or when bonded directly together, complete a —CH$_2$CH$_2$—, —CH$_2$CH$_2$CH$_2$—, or

group.

14. The herbicidal composition according to claim 9 or 10, wherein X is Br; Y is H; $R^1$ and $R^2$, when bonded directly together, complete a cyclic radical with the $R^1$ bonded $R^2$ portion being —CH$_2$—CH$_2$—CH$_2$—; and A represents

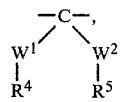

wherein $W^1$ and $W^2$ each represent —O—; and $R^4$ and $R^5$ each represent a C$_{1-4}$ alkyl group.

15. The herbicidal composition according to claim 9 which is in a form of a wettable powder, a flowable, a granule or an emulsifiable concentrate which comprises the compound (I) as an active ingredient and an inert solid or liquid carrier.

16. A method of controlling weeds in a cultivation of a crop plant by applying an effective amount of the compound (I) of claim 1.

17. The compound of claim 1, wherein X is Cl, Y and $R^1$ are hydrogen, $R^2$ is methyl and A is —CO—.

18. The compound of claim 1, wherein X is Br, Y and $R^1$ are hydrogen, $R^2$ is methyl and A is —CO—.

19. The compound of claim 1, wherein X and Y are Cl, $R^1$ is hydrogen, $R^2$ is methyl and A is —CO—.

20. The compound of claim 1, wherein X is Cl, Y is hydrogen, $R^1$ and $R^2$ are methyl, and A is —CO—.

21. The compound of claim 1, wherein X is Br, Y is hydrogen, $R^1$ and $R^2$ are methyl and A is —CO—.

22. The compound of claim 1, wherein X and Y are Cl, $R^1$ and $R^2$ are methyl and A is —CO—.

23. The compound of claim 1, wherein X is Cl, Y is hydrogen, $R^1$ is methyl, $R^2$ is phenyl and A is —CO—.

24. The compound of claim 1, wherein X is Br, Y is hydrogen, $R^1$ is methyl, $R^2$ is phenyl and A is —CO—.

25. The compound of claim 1, wherein X is Br, Y is hydrogen, $R^1$ is ethyl, $R^2$ is methyl and A is —CO—.

26. The compound of claim 1 wherein X is Cl, Y is hydrogen, $R^1$ is n-propyl, $R^2$ is methyl and A is —CO—.

27. The compound of claim 1, wherein X is Br, Y is hydrogen, $R^1$ is n-propyl, $R^2$ is methyl and A is —CO—.

28. The compound of claim 1, wherein X is Cl, Y is hydrogen, $R^1$ is n-butyl, $R^2$ is methyl and A is —CO—.

29. The compound of claim 1, wherein X is Br, Y is hydrogen, $R^1$ is n-butyl, $R^2$ is methyl and A is —CO—.

30. The compound of claim 1, wherein substituent $R^3$ is methyl and $R^6$ is alkyl selected from the group consisting of methyl, ethyl, propyl, butyl, pentyl and hexyl; allyl or propargyl; carboxy-acyl selected from the group consisting of acetyl, chloroacetyl, propionyl, butyryl, valeryl, acryloyl, methacryloyl and benzoyl; C$_{2-5}$ alkoxycarbonyl selected from the group consisting of methoxycarbonyl, ethoxycarbonyl, propoxycarbonyl, and butoxycarbonyl.

31. The herbicidal composition according to claim 9 which comprises: 5 to 80 wt% of the compound (I) as a herbicidally active ingredient in combination with a carrier.

* * * * *